United States Patent [19]

Harada et al.

[11] Patent Number: 5,115,011
[45] Date of Patent: May 19, 1992

[54] PROCESS FOR PRODUCING QUALITY-IMPROVED WATER-ABSORBENT POLYMERS AND PRODUCTS

[75] Inventors: Nobuyuki Harada; Toshihiro Okuno; Tadao Shimomura, all of Osaka, Japan

[73] Assignee: Nippon Shokubai Kagaku Kogyo Co., Ltd., Osaka, Japan

[21] Appl. No.: 481,274

[22] Filed: Feb. 20, 1990

[30] Foreign Application Priority Data

Feb. 28, 1989 [JP] Japan .................................. 1-45239
May 29, 1989 [JP] Japan ................................. 1-132576

[51] Int. Cl.$^5$ .............................................. C08K 3/30
[52] U.S. Cl. .................................... 524/419; 524/421; 524/422; 524/428; 524/436; 524/566; 524/564; 524/599
[58] Field of Search ............... 524/419, 421, 422, 428, 524/436, 437

[56] References Cited

U.S. PATENT DOCUMENTS

| | | | |
|---|---|---|---|
| 4,043,952 | 8/1977 | Ganslaw et al. . | |
| 4,043,952 | 8/1977 | Ganslaw et al. | 524/398 |
| 4,295,987 | 10/1981 | Parks . | |
| 4,587,308 | 5/1986 | Makita et al. | 525/387 |
| 4,766,173 | 8/1988 | Bailey et al. . | |
| 4,863,989 | 9/1989 | Obayashi et al. | 524/418 |

FOREIGN PATENT DOCUMENTS

| | | |
|---|---|---|
| 0031628A2 | 7/1981 | European Pat. Off. . |
| 0268459A2 | 5/1988 | European Pat. Off. . |
| 0268459 | 5/1988 | European Pat. Off. . |
| 3123922A1 | 1/1983 | Fed. Rep. of Germany . |
| 56-103208 | 8/1981 | Japan . |
| 61-97333 | 5/1986 | Japan . |
| 62-7745 | 1/1987 | Japan . |
| 63-260907 | 10/1988 | Japan . |
| 63-272349 | 11/1988 | Japan . |
| 2162525A | 2/1986 | United Kingdom . |

OTHER PUBLICATIONS

1991 American Chemical Society Article No. CA112(4):21436t.

*Primary Examiner*—John C. Bleutge
*Assistant Examiner*—Mark Sweet
*Attorney, Agent, or Firm*—Armstrong, Nikaido, Marmelstein, Kubovcik & Murray

[57] ABSTRACT

This invention relates to a process for producing a quality-improved water-absorbent polymer in which the aqueous liquid (I), which is obtained by mixing in an aqueous medium at least one kind of a water-soluble salt (A) selected from a group of halogenated compounds, sulfates, acetates, and nitrates, which are derived from at least one kind of a polyvalent metal selected from a group of aluminum, calcium, and magnesium, with at least one kind of a water-soluble salt (B) selected from a group of monovalent metal salts and ammonium salts, which are derived from at least one kind of an oxyacid selected from a group of sulfurous acid and thiosulfuric acid, is mixed with a water-absorbent polymer (II) in a proportion of that the water-soluble salt of the polyvalent metal (A) is in a range of 0.1∼10 parts by weight against 100 parts by weight of the water-absorbent polymer (II) and the water-soluble salt of the oxyacid (B) is in a range of 0.1∼10 parts by weight against 100 parts by weight of the water-absorbent polymer (II). The mixture which is obtained by mixing the aqueous liquid (I) with the water-absorbent polymer (II) has relatively-improved capacities in the fluidity and the amount of residual monomers. This invention displays a more sufficient effect by compulsorily bringing the mixture into contact with an oxygen-containing gas.

17 Claims, No Drawings

PROCESS FOR PRODUCING QUALITY-IMPROVED WATER-ABSORBENT POLYMERS AND PRODUCTS

BACKGROUND OF THE INVENTION

The present invention relates to process for producing water-absorbent polymers of improved quality which have broad utility not only for sanitary materials such as physiological napkins, paper diapers, and the like, but also in a variety of fields such as farming and gardening, foods, and the like.

In recent years, water-absorbent polymers have been used not only for sanitary materials such as physiological napkins, paper diapers, and the like, but also for materials, which require water-absorbent and water-holding properties, such as water-holding agents for use in farming and gardening.

As the water-absorbent polymers of that kind, for example, there have been known the cross-linked products of partially-neutralized polyacrylic acid, hydrolysis products of graft polymers of starch with acrylonitrile, neutralization products of graft polymers of starch with acrylic acid, saponification products of copolymers of vinyl acetate with acrylic acid esters, and hydrolysis products of copolymers of acrylonitrile or acrylamide or their cross-linked materials.

However, it has also been known that these water-absorbent polymers have a problem that, due to the known blocking phenomenon among the polymer particles under a high humidity condition, the fluidity of these particles becomes lower and handling becomes difficult. Although several attempts to improve the fluidity of these particles of water-absorbent polymers have been carried out (Japanese official patent provisional publications, showa 56-103208 and 61-97333, and U.S. Pat. No. 4,295,987), satisfactory improvement has not yet been achieved because of complications of handling and decrease of the water-absorbent capacity.

On the other hand, in the Japanese official patent provisional publication, showa 62-7745, there has been disclosed a method wherein, to prevent the blocking of particles of water-absorbent polymers, a quality-improved water-absorbent polymer is produced by spraying an aqueous solution of aluminum sulfate on a water-absorbent polymer, using an apparatus for spraying and drying. Also, in the U.S. Pat. No. 4,043,952 there has been disclosed a method wherein a quality-improved water-absorbent polymer is produced by surface treatment of the polymer particles in a dispersion medium containing a polyvalent metallic ion, such as aluminum etc. (for example, a mixed solution of methanol and water). However, there are limitations to these methods because a complex apparatus, such as an apparatus for spraying and drying, must be used, or a specialized dispersion medium must be used and, therefore, particles of a quality-improved water-absorbent polymer could not easily be obtained.

Also, in the Europian patent provisional publication 0268459A2, there has been disclosed a method wherein, to prevent deterioration and decomposition, with the passage of time for a swelling gel of a water-absorbent polymer, a quality-improved water-absorbent polymer is produced by spraying and mixing an aqueous solution of a reductive agent containing sulfur (for example, sodium thiosulfate etc.) with the water-absorbent polymer particles. However, this method does not improve the fluidity and the property for resisting blocking of a water-absorbent polymer itself.

Besides, the existence of residual unpolymerized monomers in these water-absorbent polymers, especially when such polymers are used as sanitary materials or in the field of foods, are drawing attention on a side of safety, so that several attempts to decrease the content of residual monomers have been carried out. For example, there have been proposed a method which lowers the residual monomers by adding an amino acid to a water-containing gel of a water-absorbent polymer (U.S. Pat. No. 4,766,173) and a method which lowers the residual monomers by illuminating a water-containing gel with an ultraviolet light (Japanese official patent provisional publication, showa 63-260907). However, these methods have not showed a sufficiently lowering effect on the residual monomers and, if an attempt is made to decrease the residual monomers to a standard of enough safety, a lot of investment and work is required leading to an unpractical application.

SUMMARY OF THE INVENTION

The present invention undertakes to solve said problems in the conventional art; that is, the problems are that, due to the blocking phenomenon among the polymer particles under a high humidity condition, fluidity of the particles becomes lower and handling becomes difficult, and the lowering effect on the residual monomers is not sufficient.

Thus, the object of the present invention is to provide a process for producing a water-absorbent polymer particle which shows such superior fluidity that blocking does not take place under conditions of high humidity, and which contains only a small amount of residual monomers and therefore has superior safety.

The present inventors, as a result of intensive research into said circumstances, found that said object is attained with a simple and economical means in which the water-absorbent polymer is mixed with an aqueous liquid containing a specialized water-soluble salt, and thus arrived at the present invention.

The first present invention relates to a process for producing a quality-improved water-absorbent polymer which is achieved by mixing an aqueous liquid (I), that is prepared by mixing in an aqueous medium at least one kind of a water-soluble salt (A) selected from a group of halogenated compounds, sulfates, acetates, and nitrates, which are derived from at least one kind of a polyvalent metal selected from a group of aluminum, calcium, and magnesium, with at least one kind of a water-soluble salt (B) selected from a group of monovalent metal salts and ammonium salts, which are derived from at least one kind of an oxyacid selected from the group of sulfurous acid and thiosulfuric acid, with a water-absorbent polymer (II) in a proportion such that the water-soluble polyvalent metal salt (A) is 0.1 ~ 10 parts by weight per 100 parts of the water-absorbent polymer (II), and the water-soluble oxyacid salt (B) is 0.1 ~ 10 parts by weight per the same 100 parts of polymer.

Furthermore, a second aspect of the present invention relates to a process for producing a quality-improved water-absorbent polymer which is achieved by mixing an aqueous liquid (I), that is prepared by mixing in an aqueous medium at least one kind of a water-soluble salt (A) selected from a group of halogenated compounds, sulfates, acetates, and nitrates, which are derived from at least one kind of a polyvalent metal selected from a group of aluminum, calcium, and magnesium, with at least one kind of a water-soluble salt (B) selected from a group of monovalent metal salts and ammonium salts, which are derived from at least one kind of an oxyacid selected from the group of sulfurous acid and thiosulfuric acid, with a water-absorbent polymer (II) in a proportion that the water-soluble polyvalent metal salt (A) is 0.1~10 parts by weight against 100 parts of the water-absorbent polymer (II) and the water-soluble oxyacid salt (B) is 0.1~10 parts by weight against the same 100 parts, and further specialized by compulsorily bringing the thus-obtained mixture into contact with an oxygen-containing gas.

The water-absorbent polymer (II) used in this invention forms a water-containing gel (a hydrogel) by absorbing a large amount of water accompanied by swelling. For this polymer (II), for example, are cited a hydrolysis product derived from a graft copolymer of starch with acrylonitrile, a neutralization product derived from a graft copolymer of starch with acrylic acid, a saponification product derived from a copolymer of an acrylic acid ester with vinyl acetate, a hydrolysis product derived from an acrylonitrile copolymer or an acrylamide copolymer, a neutralization product derived from a polyacrylic acid of the self cross-linking type, a cross-linked product of a polyacrylic acid salt, and a neutralization product derived from a copolymer of a cross-linked isobutylene with maleic anhydride. Further, as the water-absorbent polymers of these kinds, there may be used those showing uniformity in cross-linking density or those which have been cross-linked only on a surface. Preferred is a cross-linked polymer of a water-soluble ethylenically unsaturated monomer having acrylic acid (or its salt) as a main component, but the process of this invention is not so limited.

The water-soluble salt of the polyvalent metal (A) used in this invention is at least one kind of a water-soluble salt selected from the group of halogenated compounds, sulfates, acetates, and nitrates which are derived from at least one kind of a polyvalent metal selected from the group of aluminum, calcium, and magnesium.

As concrete examples of the water-soluble salts of polyvalent metals (A) are given aluminum chloride, polyaluminum chloride, calcium chloride, magnesium chloride, aluminum sulfate, magnesium sulfate, calcium sulfate, aluminum potassium sulfate, aluminum ammonium sulfate, aluminum nitrate, calcium nitrate, magnesium nitrate, aluminum acetate, calcium acetate, and magnesium acetate these may be used alone or in combination. Among them, are preferred the water-soluble salts of aluminum which are great in their fluidity-improving effect on the water-absorbent polymer and which have a lowering effect on the content of residual monomers.

The amount of the water-soluble salts of polyvalent metals (A) used is in a range of 0.1~10 parts by weight per 100 parts of the water-absorbent polymer (II). If less than 0.1 part by weight is used, the fluidity-improving effect and the lowering effect on the residual monomers become insufficient and, if the amount is so large as exceeding 10 parts by weight, the effect on the polymer does not correspond to the amount used and because, conversely, the water-absorbing capacity of the water-absorbent polymer decreases.

The water-soluble salt of the oxyacid (B) used in this invention is at least one kind of a water-soluble salt selected from the group of monovalent metal salts and ammonium salts, which are derived from at least one kind of an oxyacid selected from the group of sulfurous acid and thiosulfuric acid. As concrete examples of the water-soluble salts of the oxyacids (B) are given sodium sulfite, sodium hydrogen sulfite, sodium thiosulfate, potassium sulfite, ammonium sulfite, potassium hydrogen sulfite, ammonium hydrogen sulfite, ammonium thiosulfate, and potassium thiosulfate. These can be used by alone or in combination.

The amount of the water-soluble salts of oxyacids (B) used is in a range of 0.1~10 parts by weight per 100 parts by weight of the water-absorbent polymer. If less than 0.1 part by weight is used, the fluidity-improving effect or the lowering effect on the residual monomers become insufficient and, if the amount is so large as exceeding 10 parts by weight, it is unfavorable because an effect corresponding to the amount used can not be obtained.

An important point to attain the object of this invention is to mix the water-soluble polyvalent metal salt (A) and the water-soluble salt of an oxyacid (B) with the water-absorbent polymer (II) in an aqueous liquid (I), which is obtained by mixing the metal salt (A) with the salt of an oxyacid (B) in an aqueous medium.

Therefore, the effect of this invention is not obtained when the water-soluble polyvalent metal salt (A) and the water-soluble salt of an oxyacid (B) are first mixed with the water-absorbent polymer in a dry state, and then, water is added; a method in which either one of said water-soluble salts (A) and (B) is mixed with the water-absorbent polymer in a dry state and then an aqueous solution containing the other water-soluble salt is added; or a method in which an aqueous solution containing either one of said water-soluble salts (A) and (B) is added to the water-absorbent polymer and then, the other water-soluble salt is mixed therewith in a dry state.

To obtain the aqueous liquid (I) used in this invention, for example, are cited a method in which the water-soluble polyvalent metal salt (A) and the water-soluble salt of an oxyacid (B) are beforehand added and mixed into an aqueous medium, and a method in which an aqueous solution of the water-soluble polyvalent metal salt (A) and an aqueous solution of the water-soluble salt of an oxyacid (B) are beforehand separately prepared and then, these solutions are mixed to prepare the mixed aqueous liquid (I).

Although the amount of the aqueous liquid (I) which is mixed with the water-absorbent polymer (II) varies according to the amount of said water-soluble salts (A) and (B) which are contained in the aqueous liquid (I), it is usually in a range of 1~120 parts by weight, more preferably 10~60 parts by weight, per 100 parts of the water-absorbent polymer. If the amount of the aqueous liquid (I) is less than 1 part by weight, a uniform distribution of said water-soluble salts (A) and (B) into effective contact with the water-absorbent polymer (II) is difficult to achieve and the decrease of the residual monomers and increase in the fluidity-improving effect become insufficient. Besides, if the amount exceeds 120 parts by weight, mixing of the aqueous liquid (I) followed by drying of the aqueous medium is difficult and becomes disadvantageous in productivity.

As the aqueous medium used to obtain the aqueous liquid (I) in this invention, water, or a medium which is prepared by mixing a hydrophilic organic solvent with water, is effective. As the hydrophilic organic solvent, for example, are cited the alcohols of carbon numbers 1~4 such as methanol, ethanol, and isopropanol etc., the ketones such as acetone etc., N,N-dimethylformamide, and dimethylsulfoxide.

Furthermore, as far as the effect of this invention is not disturbed, an aqueous liquid (I) containing an oxidative agent, an oxidation-preventive agent, a reductive agent, an ultraviolet light-absorbent agent, a sterilization agent, a fungicide, manure, a perfume, or a deodorizing agent etc. is possible to use.

In order to carry out this invention for mixing the aqueous liquid (I) with the water-absorbent polymer (II), can there be adopted, for example, a method in which the water-absorbent polymer (II) is added to and mixed with the aqueous liquid (I) with mechanical stirring or with flowing in a gas current, or a method in which the water-absorbent polymer (II) is poured into, mixed and kneaded with the aqueous liquid (I). The method is not limited so long as the aqueous liquid (I) is uniformly mixed with the water-absorbent polymer (II).

As a practical apparatus which is used to mix the aqueous liquid (I) with the water-absorbent polymer (II), for example, are cited several types of mixers such as a V-shape rotating mixer, a ribbon mixer, a screw mixer, a rotary disk mixer, a pneumatic conveying mixer, a paddle mixer, and the like; kneading machines such as a kneader and the like; or various kinds of granulators such as a fluidized bed granulator, a high speed agitated granulator, a tumbling granulator, and the like.

Although the mixture which is obtained by mixing the aqueous liquid (I) with the water-absorbent polymer (II) has an improved fluidity and a reduced amount of residual monomers, the effect of this invention may further increase with warming of said mixture. To warm the mixture, for example, may be used a usual dryer such as an agitated trough dryer, a rotary dryer, a disk dryer, a kneader dryer, a fluidized bed dryer, a pneumatic conveying dryer, an infrared dryer, a hot-air dryer, a microwave dryer, and the like, and a heater.

Although the mixture which is obtained by mixing the aqueous liquid (I) with the water-absorbent polymer (II) has relatively-improved capacities in said fluidity and reduced amount of residual monomers, this invention displays a more sufficient effect by compulsorily bringing the mixture into contact with an oxygen-containing gas.

In this invention, to compulsorily bring a mixture of the aqueous liquid (I) and the water-absorbent polymer (II) into contact with an oxygen-containing gas, there are, for example, a method in which said mixture is brought into contact with the oxygen-containing gas while it is floating in the gas, and a method in which said mixture is brought into contact with the gas by agitating it with a current of an oxygen-containing gas, but the method is not limited to subjecting the mixture to compulsory contact with the oxygen-containing gas. Thus, as an apparatus which can be used favorably in order to bring the mixture into contact with the oxygen-containing gas, for example, are cited an air transporter, a pneumatic conveying dryer, a fluidized bed dryer, an air slide, and the like. Besides, by these apparatuses the mixing of the aqueous liquid (I) with the water-absorbent polymer (II) can be done at the same time.

The gas with which the mixture comes in contact in this invention must be an oxygen-containing gas. In a case of a gas which does not contain oxygen, even if it is compulsority brought into contact, any improvement in the fluidity of the water-absorbent polymer (II) and the lowering effect on the residual monomers are not displayed.

As an oxygen-containing gas used in this invention, for example, are cited an oxygen gas, a mixture gas of an inert gas, such as nitrogen, with oxygen, and a mixture gas of water on steam with oxygen. In particular, from a standpoint of economy and working efficiency is preferred air, which is a mixture of oxygen with nitrogen, etc.

Furthermore, although the temperature of the oxygen-containing gas is not limited for use in this invention, when a gas warmed to least at 20° C. is used, it is favorable because said quality-improving effect is enhanced. Besides, if an oxygen-containing gas of such high temperature as over 200° C. is used, it has been found that the water-absorbent capacity of the polymer decreases.

According to this invention, there can be produced, simply and with high efficiency, a water-absorbent polymer which does not cause blocking, even under high humidity, and is superior in fluidity, and which shows only a small amount of residual monomers. Besides, according to this invention, without any loss of the liquid-absorbent capacity which the water-absorbent polymer primarily has, said capacities can be significantly raised.

Thus, the quality-improved water-absorbent polymer which is obtained by the producing process in this invention can be suitably used for absorbing agents in sanitary materials such as a disposable diaper and a physiological napkin, for water-holding agents in medical use, for water-holding agents in farming and gardening, and for uses that requires water-absorbent and water-holding properties, such as industrial dehydrating agents etc.

DESCRIPTION OF THE INVENTION

Hereinafter, the present invention is further explained with examples, but the scope thereof is not limited to those examples. Reference example 1

A 40% aqueous solution of a series of acrylic acid monomeric salts, 4000 parts by weight, composed of 74.96 mol % of sodium acrylate, 25 mol % of acrylic acid, and 0.04 mol % of N,N'-methylenebisacrylamide, was subjected to static polymerization by using 1.0 part by weight of ammonium persulfate and 0.2 parts by weight of sodium hydrogen sulfite at 40°~90° C. under nitrogen atmosphere, whereby a polymer of a water-containing gel form was obtained. This polymer of a water-containing gel form was dried at 160° C. in a hot-air dryer, pulverized with a hammer type pulverizer, and put through a 20 mesh metal sieve, whereby a product fraction which passed 20 mesh (hereinafter referred to as [water-absorbent polymer before quality-improvement (IIa)]) was collected.

First, examples, and examples for comparison, of the first present invention are described.

EXAMPLE 1

An aqueous liquid was prepared by adding 0.6 g of aluminum sulfate and 1.5 g of sodium hydrogen sulfite into 3.0 g of deionized water followed by mixing. This aqueous liquid was added with mixing to 30 g of the water-absorbent polymer before quality-improvement (IIa) and then, dried at 80° C. for 5 minutes in a hot air-dryer (produced from Tabai.Espek Co., Ltd.), whereby the quality-improved water-absorbent polymer in the first aspect of the present invention (hereinafter, simply referred to as [water-absorbent polymer of this invention]) (1) was obtained.

EXAMPLE 2

The procedure of example 1 was repeated except that the water-absorbent polymer before quality-improvement (II a) was replaced by a water-absorbent polymer in the starch-acrylic acid graft polymer series (San Wet IM-1000, produced from Sanyo Chemical Industries Ltd., hereinafter referred to as [water-absorbent polymer before quality-improvement (II b)]) of the same amount, whereby the water-absorbent polymer of this invention (2) was obtained.

EXAMPLE 3

An aqueous liquid was prepared by adding 0.6 g of polyaluminum chloride and 1.5 g of sodium hydrogen sulfite to 3.0 g of deionized water followed by mixing. This aqueous liquid, 5.1 g, was added with mixing to 30 g of the water-absorbent polymer before quality-improvement (IIa) obtained in the reference example 1 and then, dried at 80° C. for 30 minutes in a hot-air dryer (produced from Tabai-Espek Co., Ltd.), whereby the water-absorbent polymer of this invention (3) was obtained.

EXAMPLE 4

The procedure of example 3 was repeated except that 11.1 g of an aqueous liquid obtained by changing the amount of deionized water used to 9.0 g whereby the water-absorbent polymer of this invention (4) was obtained.

EXAMPLE 5

The procedure of example 3 was repeated except that 17.1 g of an aqueous liquid obtained by changing the amount of deionized water used to 15.0 g, whereby the water-absorbent polymer of this invention (5) was obtained.

EXAMPLE 6

The procedure of example 3 was repeated except that 20.1 g of an aqueous liquid obtained by changing the amount of deionized water used to 18.0 g, whereby the water-absorbent polymer of this invention (6) was obtained.

EXAMPLE 7

An aqueous liquid was prepared by adding 0.6 g of aluminum sulfate and 0.9 g of sodium sulfite to 6.0 g of deionized water followed by mixing. This aqueous liquid was added with mixing to 30 g of the water-absorbent polymer before quality-improvement (IIa) obtained from the reference example 1 and then, dried at 120° C. for 10 minutes in a hot-air dryer (produced from Tabai-.Espek Co., Ltd.), whereby the water-absorbent polymer of this invention (7) was obtained.

EXAMPLE 8

An aqueous liquid was prepared by adding 0.6 g of aluminum sulfate and 1.5 g of sodium thiosulfate to 6.0 g of deionized water followed by mixing. This aqueous liquid was added with mixing to 30 g of the water-absorbent polymer before quality-improvement (IIa) obtained from the reference example 1 and then, dried at 120° C. for 10 minutes in a hot-air dryer (produced from Tabai.Espek Co. Ltd.), whereby the water-absorbent polymer of this invention (8) was obtained.

EXAMPLE 9

An aqueous liquid was prepared by adding 0.6 g of polyaluminum chloride and 1.5 g of sodium sulfite to 6.0 g of deionized water followed by mixing. This aqueous liquid was added with mixing to 30 g of the water-absorbent polymer before quality-improvement (IIa) obtained from the reference example 1 and then, dried at 120° C. for 10 minutes in a hot-air dryer (produced from Tabai.Especk Co.,Ltd.), whereby the water-absorbent polymer of this invention (9) was obtained.

EXAMPLE 10

An aqueous liquid was prepared by adding 0.6 g of aluminum sulfate and 1.5 g of sodium hydrogen sulfite to 6.0 g of deionized water followed by mixing. This aqueous liquid was added with mixing to 30 g of the water-absorbent polymer before quality-improvement (IIa) obtained from the reference example 1 and then, dried at 180° C. for 3 minutes in a hot-air dryer (produced from Tabai.Espek Co., Ltd.), whereby the water-absorbent polymer of this invention (10) was obtained.

EXAMPLE 11

An aqueous liquid was prepared by adding 0.03 g of polyaluminum chloride and 0.09 g of sodium hydrogen sulfite to 0.3 g of deionized water followed by mixing. This aqueous liquid was added with mixing to 30 g of the water-absorbent polymer before quality-improvement (IIa) obtained from the reference example 1, whereby the water-absorbent polymer of this invention (11) was obtained.

EXAMPLE 12

An aqueous liquid was prepared by adding 0.18 g of polyaluminum chloride and 0.3 g of sodium hydrogen sulfite to 1.5 g of deionized water followed by mixing. This aqueous liquid was added with mixing to 30 g of the water-absorbent polymer before quality-improvement (IIa) obtained from the reference example 1, whereby the water-absorbent polymer of this invention (12) was obtained.

EXAMPLE 13

An aqueous liquid was prepared by adding 0.6 g of polyaluminum chloride and 0.15 g of sodium hydrogen sulfite to 3.0 g of deionized water followed by mixing. This aqueous liquid was added with mixing to 30 g of the water-absorbent polymer before quality-improvement (IIa) obtained from the reference example 1 and then, dried at 80° C. for 5 minutes in a hot-air dryer (produced from Tabai.Espek Co., Ltd.), whereby the water-absorbent polymer of this invention (13) was obtained.

EXAMPLE 14

An aqueous liquid was prepared by adding 0.3 g of calcium chloride and 0.9 g of sodium hydrogen sulfite to 3.0 g of deionized water followed by mixing. This aqueous liquid was added with mixing to 30 g of the water-absorbent polymer before quality-improvement (IIa) obtained from the reference example 1 and then, dried at 80° C. for 15 minutes in a hot-air dryer (produced from Tabai.Espek Co., Ltd.), whereby the water-absorbent polymer of this invention (14) was obtained.

EXAMPLE 15

An aqueous liquid was prepared by adding 0.6 g of magnesium chloride and 1.5 g of sodium hydrogen sulfite to 3.0 g of deionized water followed by mixing. This aqueous liquid was added with mixing to 30 g of the water-absorbent polymer before quality-improvement (IIa) obtained from the reference example 1 and then, dried at 80° C. for 15 minutes in a hot-air dryer (produced from Tabai.Espek Co., Ltd.), whereby the water-absorbent polymer of this invention (15) was obtained.

EXAMPLE 16

An aqueous liquid was prepared by adding 1.2 g of polyaluminum chloride and 0.06 g of sodium hydrogen sulfite to 6.0 g of deionized water followed by mixing. This aqueous liquid was added with mixing to 30 g of the water-absorbent polymer before quality-improvement (IIa) obtained from the reference example 1 and then, dried at 120° C. for 5 minutes in a hot-air dryer (produced from Tabai.Espek Co., Ltd.), whereby the water-absorbent polymer of this invention (16) was obtained.

EXAMPLE 17

An aqueous liquid was prepared by adding 1.8 g of polyaluminum chloride and 0.06 g of sodium hydrogen sulfite to 12.0 g of deionized water followed by mixing. This aqueous liquid was added with mixing to 30 g of the water-absorbent polymer before quality-improvement (IIa) obtained from the reference example 1 and then, dried at 120° C. for 10 minutes in a hot air-dryer (produced from Tabai.Espek Co., Ltd.), whereby the water-absorbent polymer of this invention (17) was obtained.

EXAMPLE 18

An aqueous liquid was prepared by adding 3.0 g of polyaluminum chloride and 0.06 g of sodium sulfite to 12.0 g of deionized water followed by mixing. This aqueous liquid was added with mixing to 30 g of the water-absorbent polymer before quality-improvement (IIa) obtained from the reference example 1 and then, dried at 120° C. for 10 minutes in a hot-air dryer (produced from Tabai.Espek Co., Ltd.), whereby the water-absorbent polymer of this invention (18) was obtained.

EXAMPLE 19

An aqueous liquid was prepared by adding 0.6 g of polyaluminum chloride and 0.15 g of sodium hydrogen sulfite to 6.0 g of deionized water followed by mixing. This aqueous liquid was added with mixing to 30 g of the water-absorbent polymer before quality-improvement (IIa) obtained from the reference example 1 and then, dried at 150° C. for 5 minutes in a hot-air dryer (produced from Tabai.Espek Co., Ltd.), whereby the water-absorbent polymer of this invention (19) was obtained.

EXAMPLE 20

An aqueous liquid was prepared by adding 0.6 g of aluminum sulfate and 1.5 g of potassium sulfite to 7.5 g of deionized water followed by mixing. This aqueous liquid was added with mixing to 30 g of the water-absorbent polymer before quality-improvement (IIa) obtained from the reference example 1 and then, dried at 120° C. for 15 minutes in a hot-air dryer (produced from Tabai.Espek Co., Ltd.), whereby the water-absorbent polymer of this invention (20) was obtained.

EXAMPLE 21

The procedure of example 20 was repeated except that the same amount of ammonium sulfite was used instead of potassium sulfite, whereby the water-absorbent polymer of this invention (21) was obtained.

EXAMPLE 22

The procedure of example 20 was repeated except that the same amount of potassium hydrogen sulfite was used instead of potassium sulfite, whereby the water-absorbent polymer of this invention (22) was obtained.

EXAMPLE 23

The procedure of example 20 was repeated except that the same amount of ammonium hydrogen sulfite was used instead of potassium sulfite, whereby the water-absorbent polymer of this invention (23) was obtained.

EXAMPLE 24

The procedure of example 20 was repeated except that the same amount of potassium thiosulfate was used instead of potassium sulfite, whereby the water-absorbent polymer of this invention (24) was obtained.

EXAMPLE 25

An aqueous liquid was prepared by adding followed by mixing 1.2 g of polyaluminum chloride and 0.06 g of sodium hydrogen sulfite to 7.0 g of an aqueous medium composed of a mixture of 6.0 g of deionized water and 1.0 g of ethanol. This aqueous liquid was added with mixing to 30 g of the water-absorbent polymer before quality-improvement (IIa) and then, dried at 120° C. for 5 minutes in a hot-air dryer (produced from Tabai.Espek Co., Ltd.), whereby the water-absorbent polymer of this invention (25) was obtained.

EXAMPLE 26

A solution was prepared by adding 0.6 g of polyaluminum chloride to 4.5 g of deionized water and another solution was separately prepared by adding 1.5 g of sodium hydrogen sulfite to 4.5 g of deionized water, and the two solution were mixed to get an aqueous liquid containing polyaluminum chloride and sodium hydrogen sulfite. This aqueous liquid was added with mixing to 30 g of the water-absorbent polymer before quality-improvement (IIa) and then, dried at 80° C. for 30 minutes in a hot-air dryer (produced from Tabai.Espek Co., Ltd.), whereby the water-absorbent polymer of this invention (26) was obtained.

EXAMPLE 27

An aqueous liquid was prepared by adding 0.6 g of aluminum acetate and 1.5 g of sodium hydrogen sulfite to 6.0 g of deionized water followed by mixing. This aqueous liquid was added with mixing to 30 g of the water-absorbent polymer before quality-improvement (IIa) obtained from the reference example 1 and then, dried at 80° C. for 15 minutes in a hot-air dryer (produced from Tabai.Espek Co., Ltd.), whereby the water-absorbent polymer of this invention (27) was obtained.

EXAMPLE 28

The procedure of example 27 was repeated except that the same amount of aluminum nitrate was used instead of aluminum acetate, whereby the water-absorbent polymer of this invention (28) was obtained.

EXAMPLE FOR COMPARISON 1

To 30 g of the water-absorbent polymer before quality-improvement (IIa) obtained from the reference example 1 were added with mixing in a dry system 0.6 g of aluminum sulfate and 1.5 g of sodium hydrogen sulfite and, to the thus-obtained mixture, 2.4 g of deionized water were added and mixed. However, as gross coagulating products from the water-absorbent polymer were formed during mixing, uniform mixing could not be carried out.

EXAMPLE FOR COMPARISON 2

To 30 g of the water-absorbent polymer before quality-improvement (IIa) obtained from the reference example 1 were added with mixing 3 g of an aqueous solution containing 0.6 g of aluminum sulfate and, to the thus-obtained mixture, 1.5 g of sodium hydrogen sulfite were added with mixing. The mixture obtained was dried as carried out for example 1, whereby the water-absorbent polymer for comparison (1) was obtained.

EXAMPLE FOR COMPARISON 3

To 30 g of the water-absorbent polymer before quality-improvement (IIa) obtained from the reference example 1 were added with mixing 0.6 g of aluminum sulfate in a dry system. The mixture obtained was dried as carried out for the example 1, whereby the water-absorbent polymer for comparison (2) was obtained.

EXAMPLE FOR COMPARISON 4

To 30 g of the water-absorbent polymer before quality-improvement (IIa) obtained from the reference example 1 were added with mixing 1.8 g of an aqueous solution containing 0.6 g of aluminum sulfate and, to the thus-obtained mixture, 2.7 g of an aqueous solution containing 1.5 g of sodium hydrogen sulfite were added with mixing. However, as gross coagulating products from the water-absorbent polymer were formed, uniform mixing was not possible.

EXAMPLE FOR COMPARISON 5

To 30 g of the water-absorbent polymer before quality-improvement (IIa) obtained from the reference example 1 were added 0.6 g of aluminum sulfate and 1.5 g of sodium hydrogen sulfite and mixed in a dry system, whereby the water-absorbent polymer for comparison (3) was obtained.

EXAMPLE FOR COMPARISON 6

To 30 g of the water-absorbent polymer before quality-improvement (IIa) obtained from the reference example 1 were added 1.5 g of sodium hydrogen sulfite and mixed in a dry system, whereby the water-absorbent polymer for comparison (4) was obtained.

EXAMPLE FOR COMPARISON 7

To 30 g of the water-absorbent polymer before quality-improvement (IIa) obtained from the reference example 1 were added with mixing 3.9 g of an aqueous solution containing 1.5 g of sodium hydrogen sulfite. However, as gross coagulating products from the water-absorbent polymer were formed, uniform mixing was not possible.

EXAMPLE FOR COMPARISON 8

To 30 g of the water-absorbent polymer before quality-improvement (IIa) were added with mixing 2.7 g of an aqueous solution containing 0.6 g of aluminum sulfate. The mixture obtained was warmed as carried out for example 1, whereby the water-absorbent polymer for comparison (5) was obtained.

EXAMPLE 29

The water-absorbent polymers (1)~(28) of the present invention which were obtained from the examples 1~28, the water-absorbent polymers for comparison (1)~(5) which were obtained from the examples for comparison 2, 3, 5, 6, and 8, the water-absorbent polymer before quality-improvement (IIa) which was obtained from the reference example 1, and the water-absorbent polymer before quality-improvement (IIb) which was used in the example 2, each of all those was evaluated, according to the procedure described below, for the amount of absorbing physiological saline, fluidity, and the amount of residual monomers.

The results are shown in Table 1.

METHOD FOR EVALUATION

1) Amount of absorbing physiological saline: Into a bag of a tea bag type (40 mm×150 mm) made of a nonwoven fablic are uniformly placed about 0.2 g of a water-absorbent polymer and immersed in an excess of physiological saline (water which contains 0.9% of sodium chloride), thereby the polymer is sufficiently swelled and then, the tea bag containing a swelled gel is taken up for 5 seconds, subjected to drain for 10 seconds on 24 sheets of toilet papers (57 mm×50 mm, 19 g/m$^2$), and weighted. The weight after the water-absorption treatment of only the bag of a tea bag type is taken as a blank and the amount of water absorption by a water-absorbent polymer is calculated according to the following equation.

$$\text{Amount of water absorption of physiological saline (g/g polymer)} = \frac{\text{Amount by weight of water absorbed (g)} - \text{Blank (g)}}{\text{Amount of water-absorbent polymer (g)}}$$

2) FLUIDITY

Into an aluminum cup of 55 mm in diameter is put 1 g of a water-absorbent polymer, spread uniformly, and stood at 37° C. with 90% of relative humidity in an air-conditioning equipment, whereby after standing for 1, 3, and 5 minutes the fluidity (presence or absence of blocking) and an attaching character to the aluminum cup are evaluated. The evaluation are carried out at the four stages according to the following standards.

double circles: no blocking product, good fluidity, and no attachment to the aluminum cup single circle: the blocking product in less than 30%, a slight attachment to the aluminum cup triangle: the blocking product in 30~70%, a small amount of attachments to the aluminum cup cross: the blocking product in 70% or more, attachments to the aluminum cup

3) AMOUNT OF RESIDUAL MONOMERS

In a 2 L beaker is precisely weighted 1.0 g of a water-absorbent polymer and to this is added 1 L of deionized water and the thus-obtained mixture is stirred for 2 hours, thereby the water-absorbent polymer is swelled.

After swelling, a hydrated gel of the water-absorbent polymer is taken by filtration using a filter paper (a Toyo filter paper No. 2) and the filtrate is analyzed with a high speed liquid chromatography.

On the other hand, a measuring line, which is obtained with a similar analysis of a standard monomer solution showing an already-known concentration, is taken as an outside standard and thus, the amount of residual monomers in a water-absorbent polymer is determined with consideration of diluting magnification of the filtrate.

EXAMPLE 30

An aqueous liquid which was prepared by adding 6 g of polyaluminum chloride and 15 g of sodium hydrogen sulfite to 30 g of deionized water followed by mixing, was added to 300 g of the water-absorbent polymer before quality-improvement (IIa) obtained from the reference example 1 and mixed.

The obtained mixture was put into a fluidized bed dryer (made from Fuji Sanyo Co., Ltd.) and brought into contact with air for 30 minutes by floating itself in air by an air current of 80° C. (a current amount of 1 m³/min.), whereby the quality-improved water-absorbent polymer in the second present invention (hereinafter referred to as [quality-improved water-absorbent polymer]) (29) was obtained.

EXAMPLE 31

The procedure of example 30 was repeated except that the same amount of the water-absorbent polymer before quality-improvement (IIb) was used instead of the water-absorbent polymer before quality-improvement (IIa) in the example 30, whereby the quality-improved water-absorbent polymer (30) was obtained.

EXAMPLE 32

An aqueous liquid which was prepared by adding 6 g of polyaluminum chloride and 15 g of sodium sulfite to

TABLE 1

| Water-absorbent polymer used for evaluation | Absorption amount of physiological saline (g/g polymer) | Fluidity after 1 min. | Fluidity after 3 min. | Fluidity after 5 min. | Amount of residual monomers (ppm) |
|---|---|---|---|---|---|
| Water-absorbent polymer of this invention | | | | | |
| (1) | 47 | ☉ | ☉ | ☉ | 88 |
| (2) | 67 | ☉ | ☉ | ☉ | 230 |
| (3) | 46 | ○ | ○ | ○ | 99 |
| (4) | 46 | ○ | ○ | ○ | 23 |
| (5) | 48 | ○ | ○ | ☉ | 39 |
| (6) | 46 | ○ | ○ | ○ | 21 |
| (7) | 47 | ○ | ○ | ○ | 72 |
| (8) | 47 | ○ | ○ | ○ | 90 |
| (9) | 47 | ○ | ○ | ○ | 64 |
| (10) | 48 | ☉ | ○ | ○ | 105 |
| (11) | 47 | ☉ | ○ | ○ | 200 |
| (12) | 48 | ○ | ○ | ○ | 150 |
| (13) | 47 | ○ | ○ | ○ | 55 |
| (14) | 44 | ○ | ○ | ○ | 121 |
| (15) | 43 | ○ | ○ | ☉ | 107 |
| (16) | 47 | ○ | ○ | ○ | 98 |
| (17) | 46 | ○ | ○ | ○ | 68 |
| (18) | 45 | ○ | ○ | ○ | 75 |
| (19) | 46 | ○ | ○ | ☉ | 48 |
| (20) | 46 | ○ | ○ | ○ | 83 |
| (21) | 46 | ○ | ○ | ○ | 51 |
| (22) | 46 | ○ | ○ | ○ | 77 |
| (23) | 46 | ○ | ○ | ○ | 59 |
| (24) | 46 | ○ | ○ | ○ | 88 |
| (25) | 46 | ○ | ○ | ○ | 76 |
| (26) | 46 | ☉ | ○ | ○ | 20 |
| (27) | 43 | ○ | ○ | ○ | 110 |
| (28) | 45 | ○ | ○ | ○ | 125 |
| Water-absorbent polymer for comparison | | | | | |
| (1) | 39 | ○ | △ | X | 460 |
| (2) | 39 | ○ | △ | X | 470 |
| (3) | 39 | △ | X | X | 480 |
| (4) | 45 | X | X | X | 470 |
| (5) | 39 | ○ | △ | X | 460 |
| Water-absorbent polymer before quality-improvement | | | | | |
| (IIa) | 45 | X | X | X | 490 |
| (IIb) | 64 | X | X | X | 1080 |

As seen in table 1, the quality-improved water-absorbent polymers obtained from the methods in this invention maintained fluidity even under a high humidity condition and displayed almost no attachment against a metal surface. Besides, the amount of the residual monomers in the quality-improved water-absorbent polymers obtained from the methods in this invention was quite fewer compared to the water-absorbent polymers before quality-improvement and the water-absorbent polymers for comparison obtained from the other methods.

Next, examples and examples for comparison in the second present invention are described.

60 g of deionized water followed by mixing, was added to 300 g of the water-absorbent polymer before quality-improvement (IIa) obtained from the reference example 1 and mixed.

The obtained mixture was put into a fluidized bed dryer and brought into contact with air for 30 minutes by floating itself in air by an air current of 40° C. (a current amount of 1 m$^3$/min.), whereby the quality-improved water-absorbent polymer (31) was obtained.

EXAMPLE 33

The procedure of example 30 was repeated except that 111 g of an aqueous liquid, which was obtained by changing the amount of deionized water used in the example 30 into 90 g, were used, whereby the quality-improved water-absorbent polymer (32) was obtained.

EXAMPLE 34

The procedure of example 30 was repeated except that 171 g of an aqueous liquid, which was obtained by changing the amount of deionized water used in the example 30 into 150 g, were used, whereby the quality-improved water-absorbent polymer (33) was obtained.

EXAMPLE 35

The procedure of example 30 was repeated except that 201 g of an aqueous liquid, which was obtained by changing the amount of deionized water used in the example 30 into 180 g, were used, whereby the quality-improved water-absorbent polymer (34) was obtained.

EXAMPLE 36

An aqueous liquid which was prepared by adding 6 g of aluminum sulfate and 9 g of sodium hydrogen sulfite to 60 g of deionized water followed by mixing, was added to 300 g of the water-absorbent polymer before quality-improvement (IIa) obtained from the reference example 1 and mixed.

The mixture obtained was put into a fluidized bed dryer and brought into contact with air for 30 minutes by floating itself in air by an air current of 60° C. (a current amount of 1 m$^3$/min.), whereby the quality-improved water-absorbent polymer (35) was obtained.

EXAMPLE 37

An aqueous liquid which was prepared by adding 6 g of aluminum sulfate and 15 g of sodium thiosulfate to 60 g of deionized water followed by mixing, was added to 300 g of the water-absorbent polymer before quality-improvement (IIa) obtained from the reference example 1 and mixed.

The mixture obtained was put into a fluidized bed dryer and brought into contact with air for 30 minutes by floating itself in air by an air current of 60° C. (a current amount of 1 m$^3$/min.), whereby the quality-improved water-absorbent polymer (36) was obtained.

EXAMPLE 38

An aqueous liquid, which was prepared by adding 6 g of aluminum chloride and 15 g of sodium thiosulfate to 60 g of deionized water followed by mixing, was added to 300 g of the water-absorbent polymer before quality-improvement (IIa) obtained from the reference example 1 and mixed.

The mixture obtained was put into a fluidized bed dryer and brought into contact with air for 10 minutes by floating itself in air by an air current of 120° C. (a current amount of 1 m$^3$/min.), whereby the quality-improved water-absorbent polymer (37) was obtained.

EXAMPLE 39

An aqueous liquid, which was prepared by adding 6 g of aluminum sulfate and 15 g of sodium hydrogen sulfite to 24 g of deionized water followed by mixing, was added to 300 g of the water-absorbent polymer before quality-improvement (IIa) obtained from the reference example 1 and mixed.

The mixture obtained was put into a fluidized bed dryer and brought into contact with air for 10 minutes by floating itself in air by an air current of 40° C. (a current amount of 2 m$^3$/min.), whereby the quality-improved water-absorbent polymer (38) was obtained.

EXAMPLE 40

An aqueous liquid, which was prepared by adding 0.3 g of polyaluminum chloride and 0.9 g of sodium hydrogen sulfite to 3.0 g of deionized water followed by mixing, was added to 300 g of the water-absorbent polymer before quality-improvement (IIa) obtained from the reference example 1 and mixed.

The mixture obtained was put into a fluidized bed dryer and brought into contact with air for 5 minutes by floating itself in air by an air current of 25° C. (a current amount of 1 m$^3$/min.), whereby the quality-improved water-absorbent polymer (39) was obtained.

EXAMPLE 41

An aqueous liquid was prepared by adding 1.8 g of polyaluminum chloride and 3.0 g of sodium hydrogen sulfite to 15 g of deionized water followed by mixing. This aqueous liquid was added to 300 g of the water-absorbent polymer before quality-improvement (IIa) obtained from the reference example 1 and mixed.

The mixture obtained was brought into contact with air as carried out in the example 40, whereby the quality-improved water-absorbent polymer (40) was obtained.

EXAMPLE 42

An aqueous liquid was prepared by adding 6.0 g of polyaluminum chloride and 1.5 g of sodium hydrogen sulfite to 30 g of deionized water followed by mixing. The obtained aqueous liquid was added with mixing to 300 g of the water-absorbent polymer before quality-improvement (IIa) obtained from the reference example 1.

The mixture obtained was put into a fluidized bed dryer and brought into contact with air for 5 minutes while it is floating in air by an air current of 80° C. (a current amount of 1 m$^3$/min.), whereby the quality-improved water-absorbent polymer (41) was obtained.

EXAMPLE 43

An aqueous liquid was prepared by adding 3 g of calcium chloride and 9 g of sodium hydrogen sulfite to 30 g of deionized water followed by mixing. This aqueous liquid was added with mixing to 300 g of the water-absorbent polymer before quality-improvement (IIa) obtained from the reference example 1.

The mixture obtained was put into a fluidized bed dryer and brought into contact with air for 15 minutes while it is floating in air by an air current of 80° C. (a current amount of 1 m$^3$/min.), whereby the quality-improved water-absorbent polymer (42) was obtained.

EXAMPLE 44

An aqueous liquid was prepared by adding 6 g of magnesium chloride and 15 g of sodium hydrogen sulfite to 30 g of deionized water followed by mixing. This aqueous liquid was added with mixing to 300 g of the water-absorbent polymer before quality-improvement (IIa) obtained from the reference example 1.

The mixture obtained was brought into contact with air as carried out in the example 43, whereby the quality-improved water-absorbent polymer (43) was obtained.

EXAMPLE 45

An aqueous liquid was prepared by adding 12 g of polyaluminum chloride and 0.6 g of sodium hydrogen sulfite to 60 g of deionized water followed by mixing. This aqueous liquid was added with mixing to 300 g of the water-absorbent polymer before quality-improvement (IIa) obtained from the reference example 1.

The mixture obtained was put into a fluidized bed dryer and brought into contact with air for 5 minutes while it is floating in air by an air current of 120° C. (a current amount of 1 m$^3$/min.), whereby the quality-improved water-absorbent polymer (44) was obtained.

EXAMPLE 46

An aqueous liquid was prepared by adding 18 g of polyaluminum chloride and 0.6 g of sodium hydrogen sulfite to 120 g of deionized water followed by mixing. This aqueous liquid was added with mixing to 300 g of the water-absorbent polymer before quality-improvement (IIa) obtained from the reference example 1.

The mixture obtained was put into a fluidized bed dryer and brought into contact with air for 10 minutes while it is floating in air by an air current of 120° C. (a current amount of 1 m$^3$/min.), whereby the quality-improved water-absorbent polymer (45) was obtained.

EXAMPLE 47

An aqueous liquid was prepared by adding 30 g of polyaluminum chloride and 0.6 g of sodium sulfite to 120 g of deionized water followed by mixing. This aqueous liquid was added with mixing to 300 g of the water-absorbent polymer before quality-improvement (IIa) obtained from the reference example 1.

The mixture obtained was brought into contact with air as carried out in the example 46, whereby the quality-improved water-absorbent polymer (46) was obtained.

EXAMPLE 48

An aqueous liquid was prepared by adding 6 g of polyaluminum chloride and 1.5 g of sodium hydrogen sulfite to 60 g of deionized water followed by mixing. This aqueous liquid was added with mixing to 300 g of the water-absorbent polymer before quality-improvement (IIa) obtained from the reference example 1.

The mixture obtained was put into a fluidized bed dryer and brought into contact with air for 5 minutes while it is floating in air by an air current of 150° C. (a current amount of 1 m$^3$/min.), whereby the quality-improved water-absorbent polymer (47) was obtained.

EXAMPLE 49

An aqueous liquid was prepared by adding 6 g of aluminum sulfate and 15 g of potassium sulfite to 75 g of deionized water followed by mixing. This aqueous liquid was added with mixing to 300 g of the water-absorbent polymer before quality-improvement (IIa) obtained from the reference example 1. The mixture obtained was put into a fluidized bed dryer and brought into contact with air for 15 minutes while it is floating in air by an air current of 120° C. (a current amount of 1 m$^3$/min.), whereby the quality-improved water-absorbent polymer (48) was obtained.

EXAMPLE 50

The procedure of example 49 was repeated except that the same amount of ammonium sulfite was used instead of potassium sulfite in example 49, whereby the quality-improved water-absorbent polymer (49) was obtained.

EXAMPLE 51

The procedure of example 49 was repeated except that the same amount of potassium hydrogen sulfite was used instead of potassium sulfite in example 49, whereby the quality-improved water-absorbent polymer (50) was obtained.

EXAMPLE 52

The procedure of example 49 was repeated except that the same amount of ammonium hydrogen sulfite was used instead of potassium sulfite in example 49, whereby the quality-improved water-absorbent polymer (51) was obtained.

EXAMPLE 53

The procedure of example 49 was repeated except that the same amount of potassium thiosulfate was used instead of potassium sulfite in example 49, whereby the quality-improved water-absorbent polymer (52) was obtained.

EXAMPLE 54

An aqueous liquid was prepared by adding 6 g of aluminum sulfate and 15 g of potassium sulfite to 75 g of deionized water followed by mixing. This aqueous liquid was added with mixing to 300 g of the water-absorbent polymer before quality-improvement (IIa) obtained from the reference example 1.

The mixture obtained was put into a fluidized bed dryer and brought into contact for 15 minutes at 120° C. with a mixture gas current of the dew point 80° C. (a current amount of 1 m$^3$/min.) composed of water steam and air while the mixture is floating in the gas by the gas current, whereby the quality-improved water-absorbent polymer (53) was obtained.

EXAMPLE 55

An aqueous liquid was prepared by adding with mixing 12 g of polyaluminum chloride and 0.6 g of sodium hydrogen sulfite to 70 g of an aqueous medium which is a mixture composed of 60 g of deionized water and 10 g of ethanol. This aqueous liquid was added with mixing to 300 g of the water-absorbent polymer before quality-improvement (IIa) obtained from the reference example 1.

The mixture obtained was put into a fluidized bed dryer and brought into contact with air for 5 minutes while it is floating in air by an air current of 120° C. (a current amount of 1 m$^3$/min.), whereby the quality-improved water-absorbent polymer (54) was obtained.

EXAMPLE 56

Two aqueous liquids were beforehand separately prepared by adding 6 g of polyaluminum chloride to 45 g of deionized water followed by mixing and by adding 15 g of sodium hydrogen sulfite to 45 g of deionized water followed by mixing. Then, these liquids were mixed to get an aqueous liquid containing polyaluminum chloride and sodium hydrogen sulfite. This aqueous liquid was added with mixing to 300 g of the water-absorbent polymer before quality-improvement (IIa) obtained from the reference example 1.

The mixture obtained was put into a fluidized bed dryer and brought into contact with air for 30 minutes while it is floating in air by an air current of 40° C. (a current amount of 1 m³/min.), whereby the quality-improved water-absorbent polymer (55) was obtained.

EXAMPLE 57

An aqueous liquid was prepared by adding with mixing 6 g of aluminum acetate and 15 g of sodium hydrogen sulfite to 60 g of deionized water. This aqueous liquid was added with mixing to 300 g of the water-absorbent polymer before quality-improvement (IIa) obtained from the reference example 1.

The mixture obtained was put into a fluidized bed dryer and brought into contact with air for 30 minutes while it is floating in air by an air current of 60° C. (a current amount of 1 m³/min.), whereby the quality-improved water-absorbent polymer (56) was obtained.

EXAMPLE 58

The procedure of example 57 was repeated except that the same amount of aluminum nitrate was used instead of aluminum acetate in example 57, whereby the quality-improved water-absorbent polymer (57) was obtained.

EXAMPLE FOR COMPARISON 9

To 300 g of the water-absorbent polymer before quality-improvement (IIa) obtained from the reference example 1 was added with mixing 36 g of an aqueous solution containing 6 g of polyaluminum chloride and, to the obtained mixture, 15 g of sodium hydrogen sulfite was added and mixed.

The mixture obtained was brought into contact with air as carried out in the example 30, whereby the water-absorbent polymer for comparison (6) was obtained.

EXAMPLE FOR COMPARISON 10

To 300 g of the water-absorbent polymer before quality-improvement (IIa) obtained from the reference example 1 were added 6 g of polyaluminum chloride and mixed in a dry system.

The mixture obtained was brought into contact with air as carried out in the example 30, whereby the water-absorbent polymer for comparison (7) was obtained.

EXAMPLE FOR COMPARISON 11

To 300 g of the water-absorbent polymer before quality-improvement (IIa) obtained from the reference example 1 were added 6 g of aluminum sulfate and 9 g of sodium hydrogen sulfite and mixed in a dry system.

The mixture obtained was brought into contact with air as carried out in the example 36, whereby the water-absorbent polymer for comparison (8) was obtained.

EXAMPLE FOR COMPARISON 12

To 300 g of the water-absorbent polymer before quality-improvement (IIa) obtained from the reference example 1 was added 9 g of sodium hydrogen sulfite and mixed in a dry system.

The mixture obtained was brought into contact with air as carried out in the example 36, whereby the water-absorbent polymer for comparison (9) was obtained.

EXAMPLE FOR COMPARISON 13

The mixture obtained in the example for comparison 8 was brought into contact with air as carried out in the example 30, whereby the water-absorbent polymer for comparison (10) was obtained.

EXAMPLE 59

The quality-improved water-absorbent polymers (29)~(57) which were obtained from the examples 30~58, the water-absorbent polymers for comparison (6)~(10) which were obtained from the examples for comparison 9~13, the water-absorbent polymer before quality-improvement (IIa) which was obtained from the reference example 1, and the water-absorbent polymer before quality-improvement (IIb) which was used in the example 31, each of all those polymers was evaluated, according to the same methods mentioned in example 29, for the amount of physiological saline absorption, the fluidity, and the amount of residual monomers.

Results are shown in Table 2.

TABLE 2

| Water-absorbent polymer used for evaluation | Absorption amount of physiological saline (g/g polymer) | Fluidity after 1 min. | Fluidity after 3 min. | Fluidity after 5 min. | Amount of residual monomers (ppm) |
| --- | --- | --- | --- | --- | --- |
| Quality-improved water-absorbent polymer | | | | | |
| (29) | 46 | ☉ | ☉ | ☉ | 14 |
| (30) | 66 | ☉ | ☉ | ☉ | 110 |
| (31) | 47 | ☉ | ☉ | ☉ | 34 |
| (32) | 46 | ☉ | ☉ | ☉ | 14 |
| (33) | 48 | ☉ | ☉ | ☉ | 8 |
| (34) | 46 | ☉ | ☉ | ☉ | 11 |
| (35) | 47 | ☉ | ☉ | ☉ | 52 |
| (36) | 48 | ☉ | ☉ | ☉ | 87 |
| (37) | 47 | ☉ | ☉ | ☉ | 33 |
| (38) | 47 | ☉ | ☉ | ☉ | 62 |
| (39) | 47 | ○ | ○ | ○ | 148 |
| (40) | 48 | ☉ | ☉ | ○ | 125 |
| (41) | 47 | ☉ | ☉ | ☉ | 37 |
| (42) | 44 | ☉ | ☉ | ○ | 91 |
| (43) | 43 | ☉ | ○ | ○ | 86 |
| (44) | 47 | ☉ | ☉ | ☉ | 72 |

TABLE 2-continued

| Water-absorbent polymer used for evaluation | Absorption amount of physiological saline (g/g polymer) | Fluidity after 1 min. | Fluidity after 3 min. | Fluidity after 5 min. | Amount of residual monomers (ppm) |
|---|---|---|---|---|---|
| (45) | 46 | ○ | ○ | ○ | 38 |
| (46) | 45 | ○ | ○ | ⊙ | 54 |
| (47) | 46 | ○ | ⊙ | ○ | 39 |
| (48) | 46 | ○ | ○ | ○ | 70 |
| (49) | 46 | ○ | ○ | ○ | 42 |
| (50) | 46 | ⊙ | ⊙ | ⊙ | 63 |
| (51) | 46 | ⊙ | ⊙ | ⊙ | 50 |
| (52) | 46 | ○ | ⊙ | ⊙ | 71 |
| (53) | 46 | ⊙ | ⊙ | ○ | 25 |
| (54) | 46 | ⊙ | ⊙ | ○ | 51 |
| (55) | 46 | ○ | ⊙ | ⊙ | 13 |
| (56) | 43 | ⊙ | ⊙ | ⊙ | 105 |
| (57) | 45 | ⊙ | ⊙ | ⊙ | 119 |
| Water-absorbent polymer for comparison | | | | | |
| (6) | 39 | ○ | △ | X | 210 |
| (7) | 41 | ○ | △ | X | 220 |
| (8) | 39 | △ | X | X | 450 |
| (9) | 41 | X | X | X | 460 |
| (10) | 39 | ○ | △ | X | 460 |
| Water-absorbent polymer before quality-improvement | | | | | |
| (IIa) | 45 | X | X | X | 490 |
| (IIb) | 64 | X | X | X | 1080 |

As seen in Table 2, the polymers which were improved in quality according to the methods in the present invention held the fluidity even under a high humidity condition and showed almost no attachment against a metal surface. Also, the amount of residual monomers in the water-absorbent polymers, which were improved in quality according to the methods in the present invention, was quite few compared to the water-absorbent polymers before quality-improvement and the water-absorbent polymers for comparison which were treated with the other methods.

What is claimed is:

1. A process for producing an improved water absorbent polymer (II), selected from the group consisting of: hydrolysis products of a graft copolymer of starch with acrylonitrile, neutralization products of a graft copolymer of starch with acrylic acid, saponification products of copolymers of an acrylic acid ester with vinyl acetate, hydrolysis products of acrylonitrile copolymers, hydrolysis products of copolymers of acrylamide, neutralization products of self cross-linked polyacrylic acids, cross-linked products of salts of polyacrylic acids, and neutralization products of cross-linked copolymers of isobutylene with maleic anhydride, which process comprises treating such polymer (II) with an aqueous liquid (I) containing:

(A) at least one water soluble salt having at least one anion (a) selected from the group consisting of: halogenated moieties, sulfates, acetates, and nitrates; and at least one polyvalent metal cation (a') selected from the group consisting of aluminum, calcium and magnesium; and (B) at least one water soluble salt having at least one anion derived from an oxyacid (b) selected from the group consisting of: sulfurous acid and thiosulfuric acid; and at least one cation (b') selected from the group consisting of: monovalent metal and ammonium;

wherein said salt (A) and said salt (B) are each present, respectively, in a proportion of about 0.1 to 10 parts by weight per 100 parts by weight of said polymer (II).

2. A process for producing the improved water-absorbent polymer as claimed in claim 1, wherein the aqueous liquid (I) is obtained by beforehand adding with mixing the water-soluble salt of the polyvalent metal (A) and the water-soluble salt of the oxyacid (B) to an aqueous medium.

3. A process for producing the improved water-absorbent polymer as claimed in claim 1, wherein the aqueous liquid (I) is obtained by beforehand separately preparing an aqueous solution of the water-soluble salt of the polyvalent metal (A) and an aqueous solution of the water-soluble salt of the oxyacid (B) respectively, and then, mixing such with one another.

4. A process for producing the improved water-absorbent polymer as claimed in claim 1, wherein the aqueous liquid (I) is mixed with the water-absorbent polymer (II) and further, is warmed.

5. A process for producing the quality-improved water-absorbent polymer as claimed in claim 1, wherein the water-soluble salt of the polyvalent metal (A) is a water-soluble salt of aluminum.

6. A process for producing the improved water-absorbent polymer as claimed in claim 1, wherein the water-soluble salt of the oxyacid (B) is an alkali metal salt.

7. A process for producing the improved water-absorbent polymer as claimed in claim 1, wherein the aqueous liquid (I) is in a range of 1 ~ 120 parts by weight per 100 parts by weight of the water-absorbent polymer (II).

8. A process for producing an improved water absorbent polymer (II) claimed in claim 1, also comprising contacting the mixture of said polymer (II) and liquid (I) with an oxygen-containing gas.

9. A process for producing the improved water-absorbent polymer as claimed in claim 8, wherein said aqueous liquid (I) is obtained by first adding with mixing said water-soluble salt of the polyvalent metal (A) and said water-soluble salt of the oxyacid (B) to an aqueous medium.

10. A process for producing the improved water-absorbent polymer as claimed in claim 8, wherein the aqueous liquid (I) is obtained by first separately preparing an aqueous solution of the water-soluble salt of the polyvalent metal (A) and an aqueous solution of the water-soluble salt of the oxyacid (B) respectively, and then, mixing such with one another.

11. A process for producing the improved water-absorbent polymer as claimed in claim 8, contacting said mixture of the aqueous liquid (I) and the water-absorbent polymer (II) with an oxygen-containing gas by passing such through said oxygen-containing gas or by agitating such in a current of the oxygen-containing gas.

12. A process for producing the improved water-absorbent polymer as claimed in claim 8, in which the oxygen-containing gas is warmed to at least 20° C.

13. A process for producing the improved water-absorbent polymer as claimed in claim 8, wherein said oxygen-containing gas is air.

14. A process for producing the improved water-absorbent polymer as claimed in claim 8, wherein said water-soluble salt of the polyvalent metal (A) is a water-soluble salt of aluminum.

15. A process for producing the improved water-absorbent polymer as claimed in claim 8, wherein said water-soluble salt of the oxyacid (B) is a salt of an alkali metal.

16. A process for producing the improved water-absorbent polymer as claimed in claim 8, wherein said aqueous liquid (I) is used in a range of 1~120 parts by weight per 100 parts by weight of the water-absorbent polymer (II).

17. The product of the process of claim 1.

* * * * *